United States Patent [19]
Bromidge

[11] Patent Number: 6,028,085
[45] Date of Patent: *Feb. 22, 2000

[54] INDOLE DERIVATIVES AS 5-HT RECEPTOR ANTAGONIST

[75] Inventor: Steven Mark Bromidge, Harlow, United Kingdom

[73] Assignee: SmithKline Beecham plc, Brentford, United Kingdom

[ * ] Notice: This patent is subject to a terminal disclaimer.

[21] Appl. No.: 09/155,589

[22] PCT Filed: Mar. 26, 1997

[86] PCT No.: PCT/EP97/01611

§ 371 Date: Sep. 30, 1998

§ 102(e) Date: Sep. 30, 1998

[87] PCT Pub. No.: WO97/37989

PCT Pub. Date: Oct. 16, 1997

[30] Foreign Application Priority Data

Apr. 4, 1996 [GB] United Kingdom .................... 9607219

[51] Int. Cl.[7] .......................... A61K 31/44; A61K 31/40; C07D 401/12; C07D 401/14; C07D 209/26
[52] U.S. Cl. .......................... 514/333; 514/339; 514/418; 514/419; 546/256; 546/278.1; 548/491
[58] Field of Search ................................ 546/278.1, 256; 514/339, 333, 418, 419; 548/491

[56] References Cited

FOREIGN PATENT DOCUMENTS

| WO 9205170 | 4/1992 | WIPO . |
| WO 9404533 | 3/1994 | WIPO . |
| WO 9422871 | 10/1994 | WIPO . |
| 95/17398 | 6/1995 | WIPO . |
| WO 9623783 | 8/1996 | WIPO . |

OTHER PUBLICATIONS

Database Crossfire, Beilstein, XP002001373.
Database Crossfire, Beilstein, XP002001374.
Database Crossfire, Beilstein, XP002001375.

*Primary Examiner*—Evelyn Huang
*Attorney, Agent, or Firm*—Soma G. Simon; William T. King; Charles M. Kinzig

[57] ABSTRACT

Prodrugs of $5HT_{2C}$ receptor antagonists of formula (I) are provided wherein the prodrug has a quaternary ammonium group, in particular quaternary pyridinium atom:

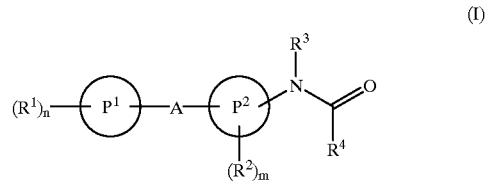

(I)

7 Claims, No Drawings

INDOLE DERIVATIVES AS 5-HT RECEPTOR ANTAGONIST

This application is the national phase of PCT/EP97/01611, filed Mar. 26, 1997.

This invention relates to compounds having pharmacological activity, processes for their preparation, to compositions containing, them and to their use in the treatment of CNS disorders.

Compounds having $5HT_{2C}$ receptor antagonist activity are known in the art. For example PCT/EP96/00368 discloses indoline derivatives as $5HT_{2C}$ antagonists.

However certain $5HT_{2C}$ receptor antagonists exhibit poor solubility which may lead to decreased activity. It has now been found that pyridinium derivatives of certain known $5HT_{2C}$ receptor antagonists show increased solubility and increased in vivo activity. It is believed that these new compounds are converted to their 'parent' compounds prior/during/or after absorption and so may increase the bioavailability of the 'parent' compound. The compounds of the invention may therefore act as prodrugs and are defined as prodrugs herein.

The present invention therefore provides, in a first aspect, a prodrug of a $5HT_{2C}$ receptor antagonist wherein the prodrug has a quaternary ammonium group, in particular a quaternary pyridinium group.

Preferably the invention provides a compound of formula (I):

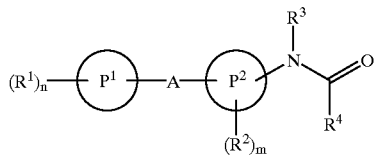

(I)

wherein:
  $R^1$ and $R^2$ groups are each independently hydrogen, $C_{1-6}$ alkyl optionally substituted by $NR^{12}R^{13}$, $C_{2-6}$ alkenyl, $C_{2-6}$ alkynyl, $C_{1-6}$ alkylthio, cyano, nitro, halogen, $CF_3$, $C_2F_5$, $NR^{12}R^{13}$, $CONR^{12}R^{13}$, $NR^{12}COR^{13}$, $S(O)_p NR^{12}R^{13}$, CHO, $OCF_3$, $SCF_3$, $COR^{14}$, $CH_2OR^{14}$, $CO_2R^{14}$ or $OR^{14}$ where p is 1 or 2 and $R^{12}$, $R^{13}$ and $R^{14}$ are independently hydrogen, $C_{1-6}$ alkyl, optionally substituted aryl or optionally substituted aryl$C_{1-6}$alkyl, or $R^1$ and $R^2$ are $N^+I^-R^{12}R^{13}CR^{12}R^{13}OCOR^{14}$ where $R^{12}$, $R^{13}$ and $R^{14}$ are as defined above and I is a counter ion;

n and m are independently 0, 1 or 2;
  $R^3$ is hydrogen or $C_{1-6}$ alkyl;
  $R^4$ is a group of formula (i):

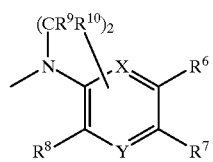

(i)

in which:
  X and Y are both nitrogen, one is nitrogen and the other is carbon or a $CR^5$ group or one is a $CR^5$ group and the other is carbon or a $CR^5$ group;

$R^5$, $R^6$, $R^7$ and $R^8$ groups are independently hydrogen, $C_{1-6}$ alkyl optionally substituted by one or more fluorine atoms, $C_{2-6}$ alkenyl, $C_{3-6}$ cycloalkyl, $C_{3-6}$ cycloalkyl$C_{1-6}$alkoxy, $C_{2-6}$ alkynyl, $C_{3-6}$ cycloalkyloxy, $C_{3-6}$ cycloalkyl-$C_{1-6}$ alkyl, $C_{1-6}$ alkylthio, $C_{3-6}$ cycloalkylthio, $C_{3-6}$ cycloalkyl-$C_{1-6}$ alkylthio, $C_{1-6}$alkoxy, hydroxy, halogen, nitro, $OCF_3$, $SCF_3$, $SO_2CF_3$, $SO_2F$, formyl, $C_{2-6}$ alkanoyl, cyano, optionally substituted phenyl or thienyl, $NR^{12}R^{13}$, $CONR^{12}R^{13}$ or $CO_2R^{14}$ where where $R^{12}$, $R^{13}$ and $R^{14}$ are as defined for $R^1$; or $R^6$ and $R^7$ form part of an optionally substituted 5- or 6-membered carbocyclic or heterocyclic ring;

$R^9$ and $R^{10}$ are independently hydrogen or $C_{1-6}$ alkyl; or
  $R^4$ is a group of formula (ii):

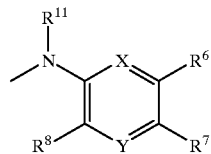

(ii)

in which X and Y are both nitrogen, one is nitrogen and the other is a $CR^5$ group or X and Y are both $CR^5$ groups and $R^5$, $R^6$, $R^7$ and $R^8$ are as defined in formula (I); and
  $R^{11}$ is hydrogen or $C_{1-6}$ alkyl, or
  $R^4$ is a group of formula (iii):

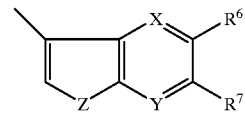

(iii)

in which $R^6$, $R^7$, X and Y are as defined in formula (i) and Z is O, S, $CH_2$ or $NR^{15}$ where $R^{15}$ is hydrogen or $C_{1-6}$ alkyl;
  $P^1$ and $P^2$ are independently phenyl, aromatic or partially saturated monocyclic or bicyclic heterocyclic rings said heterocyclic rings containing a quaternary nitrogen atom and up to two further heteroatoms selected from nitrogen, oxygen or sulphur; and
  A is a bond, a chain of 1 to 5 atoms optionally substituted by $C_{1-6}$ alkyl or A is an optionally substituted phenyl or an optionally substituted 5- to 7-membered heterocyclic ring containing up to three heteroatoms selected from nitrogen, oxygen or sulphur.

$C_{1-6}$ Alkyl groups, whether alone or as part of another group, may be straight chain or branched.

Suitably $R^1$ and $R^2$ groups are each independently hydrogen, $C_{1-6}$ alkyl optionally substituted by $NR^{12}R^{13}$, $C_{2-6}$ alkenyl, $C_{2-6}$ alkynyl, $C_{1-6}$ alkylthio, cyano, nitro, halogen, $CF_3$, $C_2F_5$, $NR^{12}R^{13}$, $CONR^{12}R^{13}$, $NR^{12}COR^{13}$, $S(O)_p NR^{12}R^{13}$, CHO, $OCF_3$, $SCF_3$, $COR^{14}$, $CH_2OR^{14}$, $CO_2R^{14}$ or $OR^{14}$ where p is 1 or 2 and $R^{12}$, $R^{13}$ and $R^{14}$ are independently hydrogen, $C_{1-6}$ alkyl, optionally substituted aryl or optionally substituted aryl$C_{1-6}$alkyl, or $R^1$ and $R^2$ are $N^+X^-$ $R^{12}R^{13}CR^{12}R^{13}OCOR^{14}$ where $R^{12}$, $R^{13}$ and $R^{14}$ are as defined above and X is a counter ion. Examples of suitable aryl groups include phenyl. Examples of suitable aryl$C_{1-6}$alkyl groups include benyl.

Preferably $R^1$ is hydrogen or methyl.

Preferably $R^2$ is hydrogen, halogen, methyl, $CF_3$ or $OCF_3$, most preferably $R^2$ is hydrogen, halogen or methyl.

Preferably $R^3$ is hydrogen.

Preferably $R^4$ is a group of formula (i). Preferably X and Y form part of a phenyl ring, that is to say one of X or Y is carbon and the other is a CH group or both of X and Y are CH groups. Most preferably $R^4$ is a group of formula (A):

(A)

in which $R^6$ and $R^7$ are as defined in formula (i).

Suitably $R^6$ and $R^7$ groups are independently hydrogen, $C_{1-6}$ alkyl optionally substituted by one or more fluorine atoms for example $CF_3$ or $C_2F_5$, $C_{2-6}$ alkenyl, $C_{3-6}$ cycloalkyl, $C_{3-6}$ cycloalkyl$C_{1-6}$alkoxy, $C_{2-6}$ alkynyl, $C_{3-6}$ cycloalkyloxy, $C_{3-6}$ cycloalkyl-$C_{1-6}$ alkyl, $C_{1-6}$ alkylthio, $C_{3-6}$ cycloalkylthio, $C_{3-6}$ cycloalkyl-$C_{1-6}$ alkylthio, $C_{1-6}$alkoxy, hydroxy, halogen, nitro, $CF_3$, $C_2F_5$, $OCF_3$, $SCF_3$, $SO_2CF_3$, $SO_2F$, formyl, $C_{2-6}$ alkanoyl, cyano, optionally substituted phenyl or thienyl, $NR^{12}R^{13}$, $CONR^{12}R^{13}$ or $CO_2R^{14}$ where $R^{12}$, $R^{13}$ and $R^{14}$ are as defined for $R^1$; or $R^6$ and $R^7$ form part of an optionally substituted 5- or 6-membered carbocyclic or heterocyclic ring. Examples of such rings include cyclopentane and dihydrofuran rings.

Preferably $R^6$ is trifluoromethyl or halogen and $R^7$ is $C_{1-6}$ alkoxy, in particular methoxy, $C_{1-6}$alkylthio, in particular methylthio or $C_{1-6}$ alkyl in particular methyl.

Suitably n and m are independently 0, 1 or 2. Preferably n is 0 or 1.

Suitably $P^1$ and $P^2$ are independently phenyl, aromatic or partially saturated monocyclic or bicyclic heterocyclic rings containing a quaternary nitrogen atom and up to two further heteroatoms selected from nitrogen, oxygen or sulphur. Preferably $P^1$ and/or $P^2$ is a quaternary group of formula (B):

(B)

where $R^{16}$ is $C_{1-6}$ alky, $C_{1-6}$ alkoxy, oxygen, $NR^{17}R^{18}$, $NHCONR^{17}R^{18}$, $NHCOR^{19}$, $CR^{17}R^{18}OCOR^{19}$, $OCR^{17}R^{18}OCOR^{19}$, $CR^{17}R^{18}OCONR^{17}R^{18}$, or $OCR^{17}R^{18}OCONR^{17}R^{18}$ where $R^{17}$, $R^{18}$ and $R^{19}$ are independently hydrogen, $C_{1-20}$ alkyl, optionally substituted aryl or optionally substituted aryl$C_{1-6}$alkyl and $I^-$ is a counter ion.

More preferably $p^1$ is a group of formula (B) where $R^{16}$ is $CR^{17}R^{18}OCOR^{19}$. Most preferably $R^{17}$ and $R^{18}$ are both hydrogen. Preferred counter ions include halogen such as chloro or iodo.

$P^2$ is preferably phenyl or pyridyl.

The urea moiety can be attached to a carbon or any available nitrogen atom of the ring $P^2$, preferably it is attached to a carbon atom. Suitable moieties when the ring $P^2$ is a 5-membered aromatic heterocyclic rings include isothiazolyl, isoxazolyl, thiadiazolyl, oxadiazolyl and triazolyl. Suitable moieties when the ring $P^2$ is a 6-membered aromatic heterocyclic rings include, for example, pyridyl, pyrimidyl or pyrazinyl. Optional substituents for $P^1$ and $P^2$ groups include those groups $R^1$ and $R^2$ listed above.

Suitably A is a bond or a chain of 1 to 5 atoms optionally substituted by $C_{1-6}$ alkyl. Examples of such chains include $(CH_2)_pE$ or $E(CH_2)_p$ where p is 1 to 4 and E is CO, O, $S(O)_x$ where x is 0 to 2 or A is NR, CONR, NRCO, NRCONR, CO, CH(OH), $C_{1-6}$alkyl, CH=CH, CH=CF, CF=CF, O, $S(O)_x$ where x is 1 or 2, NR, or $NRSO_2$ where R is hydrogen or $C_{1-6}$ alkyl. Preferably A is a bond or a group $CH_2O$, $OCH_2$, or O. Most preferably A is a bond or O.

Suitably A is an optionally substituted phenyl group or an optionally substituted 5- or 6-membered heterocyclic ring containing up to three heteroatoms selected from nitrogen, oxygen or sulphur. Preferably A is thiazolyl, isothiazolyl, oxazolyl, isoxazolyl, thiadiazolyl, triazolyl, pyridyl, pyrimidyl or pyrazinyl. Most preferably A is thiazolyl. Optional substituents when A is a phenyl or a heterocyclic group include those groups $R^1$ and $R^2$ listed above Particular compounds of the invention include:

5-Methoxy-6-trifluoromethyl-1-[3-fluoro-5-[1-(acetyloxy) methyl-pyridinium-3-yl]phenylcarbamoyl]indoline chloride, 5-Methoxy-6-trifluoromethyl-1-[3-fluoro-4-methyl-5-[1-(acetyloxy) methylpyridinium-3-yl]phenylcarbamoyl] indoline chloride, 5,6-Dichloro-1-[6-[1-(acetyloxy)methyl-2-methylpyridinium-3-yl-oxy]pyridin-3-ylcarbamoyl] indoline, and 5-Methoxy-6-trifluoromethyl-1-[3,4-difluro-5-[1-(acetyloxymethyl)pyridinium-3-yl]phenylcarbamoyl] indoline choloride.

Certain compounds of formula (I) are capable of existing in stereoisomeric forms including enantiomers and the invention extends to each of these stereoisomeric forms and to mixtures thereof including racemates. The different stereoisomeric forms may be separated one from the other by the usual methods, or any given isomer may be obtained by stereospecific or asymmetric synthesis. The invention also extends to any tautomeric forms and mixtures thereof.

The present invention also provides a process for the preparation of a compound of formula (I) or a pharmaceutically acceptable salt thereof, which process comprises (a) for compounds of formula (I) where $P^1$ and/or $P^2$ are a group of formula (B) reaction of a compound of formula (II):

(II)

in which A, $R^{1, R2}$, $R^3$, $R^4$ n and m are as defined in formula (I) and $P^{1'}$ and $P^{2'}$ are independently phenyl, aromatic or partially saturated monocyclic or bicyclic heterocyclic rings containing up to three heteroatoms selected from nitrogen, oxygen or sulphur, with a compound of formula (III):

$$I—R^{16}$$ (III)

in which $R^{16}$ is as defined in formula (I) and I is a leaving group.

The reaction of compounds (II) and (III) is preferably carried out in an inert solvent such as acetonitrile in the presence of a boron coupling reagent such as tetraphenylboron. Preferably I is a leaving group such as halogen.

Those skilled in the art will appreciate that it may be necessary to protect certain reactive groups in compounds of formulae (II) and (III) during the coupling reaction. Suitable protecting groups and methods for their attachment and removal are conventional in the art of organic chemistry, such as those described in Greene T. W. 'Protective groups in organic synthesis' New York, Wiley (1981).

Compounds of formula (I) and their pharmaceutically acceptable salts have $5HT_{2B/2C}$ receptor antagonist activity and are believed to be of potential use for the treatment or prophylaxis of CNS disorders such as anxiety, depression, epilepsy, obsessive compulsive disorders, migraine, Alzheimers disease, sleep disorders, feeding disorders such as anorexia and bulimia, panic attacks, withdrawal from drug abuse such as cocaine, ethanol, nicotine and benzodiazepines, schizophrenia, and also disorders associated with spinal trauma and/or head injury such as hydrocephalus. Compounds of the invention are also expected to be of use in the treatment of certain GI disorders such as IBS as well as microvascular diseases such as macular oedema and retinopathy.

Thus the invention also provides a compound of formula (I) for use as a therapeutic substance, in particular in the treatment or prophylaxis of the above disorders.

The invention further provides a method of treatment or prophylaxis of the above disorders, in mammals including humans, which comprises administering to the sufferer a therapeutically effective amount of a compound of formula (I).

In another aspect, the invention provides the use of a compound of formula (I) in the manufacture of a medicament for the treatment or prophylaxis of the above disorders.

The present invention also provides a pharmaceutical composition, which comprises a compound of formula (I) and a pharmaceutically acceptable carrier.

A pharmaceutical composition of the invention, which may be prepared by admixture, suitably at ambient temperature and atmospheric pressure, is usually adapted for oral, parenteral or rectal administration and, as such, may be in the form of tablets, capsules, oral liquid preparations, powders, granules, lozenges, reconstitutable powders, injectable or infusable solutions or suspensions or suppositories. Orally administrable compositions are generally preferred.

Tablets and capsules for oral administration may be in unit dose form, and may contain conventional excipients, such as binding agents, fillers, tabletting lubricants, disintegrants and acceptable wetting agents. The tablets may be coated according to methods well known in normal pharmaceutical practice.

Oral liquid preparations may be in the form of, for example, aqueous or oily suspension, solutions, emulsions, syrups or elixirs, or may be in the form of a dry product for reconstitution with water or other suitable vehicle before use. Such liquid preparations may contain conventional additives such as suspending agents, emulsifying agents, non-aqueous vehicles (which may include edible oils), preservatives, and, if desired, conventional flavourings or colourants.

For parenteral administration, fluid unit dosage forms are prepared utilising a compound of the invention or pharmaceutically acceptable salt thereof and a sterile vehicle. The compound, depending on the vehicle and concentration used, can be either suspended or dissolved in the vehicle. In preparing solutions, the compound can be dissolved for injection and filter sterilised before filling into a suitable vial or ampoule and sealing. Advantageously, adjuvants such as a local anaesthetic, preservatives and buffering agents are dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilization cannot be accomplished by filtration. The compound can be sterilised by exposure to ethylene oxide before suspension in a sterile vehicle. Advantageously, a surfactant or wetting agent is included in the composition to facilitate uniform distribution of the compound.

The composition may contain from 0.1% to 99% by weight, preferably from 10 to 60% by weight, of the active material, depending on the method of administration.

The dose of the compound used in the treatment of the aforementioned disorders will vary in the usual way with the seriousness of the disorders, the weight of the sufferer, and other similar factors. However, as a general guide suitable unit doses may be 0.05 to 1000 mg, more suitably 0.05 to 20.0 mg, for example 0.2 to 5 mg; and such unit doses may be administered more than once a day, for example two or three a day, so that the total daily dosage is in the range of about 0.5 to 100 mg; and such therapy may extend for a number of weeks or months.

When administered in accordance with the invention, no unacceptable toxicological effects are expected with the compounds of the invention.

The following Descriptions and Examples illustrate the preparation of compounds of the invention.

EXAMPLE 1

5-Methoxy-6-trifluoromethyl-1-[3-fuoro-5-[1-(acetyloxy)methyl-pyridinium-3- yl]phenylcarbamoyl]indoline chloride (E1)

To a solution of 5-methoxy-6-trifluoromethyl-1-[3-fluoro-5-(pyridin-3-yl)phenylcarbamoyl]indoline (0.5 g, 1.16 mmol) in acetonitrile (20 ml) was added sodium tetraphenylboron (0.48 g, 1.40 mmol) followed by bromomethyl acetate (0.14 ml, 1.43 mmol). The resulting mixture was heated at reflux under argon for 4 h, then cooled to room temperature, and filtered through a kieselgühr pad. The filtrate was concentrated to give the pyridinium tetraphenylborate salt as a yellow solid which was taken-up in acetonitrile/2-propanol (20 ml; 1:1 v/v) and passed through an ion-exchange column (2×10 cm of Dowex 1×2 chloride, 50–100 mesh) at ca. 1 ml/min. The eluant was concentrated, and the resulting solid was triturated with diethyl ether to give after drying the title compound (E1) as a yellow solid (0.63 g, 100%) m.p. 145–150° C.

$^1$H NMR (400 MHz; DMSO) δ: 2.18 (3H, s), 3.29 (2H, t, J=8 Hz), 3.85 (3H, s), 4.27 (2H, t, J=8 Hz), 6.50 (2H, s), 7.24 (1H, s), 7.44 (1H, m, J=10 Hz), 7.72 (1H, m, J=11 Hz), 8.09 (1H, s), 8.14 (1H, s), 8.34 (1H, dd, J=11 Hz, 7 Hz), 8.99 (1H, d, J=10 Hz), 9.23 (2H, m), 9.59 (1H, s).

Mass spectrum (FAB) 504 (M$^+$).

EXAMPLE 2

5-Methoxy-6-trifluoromethyl-1-[3-fluoro-4-methyl-5-[1-(acetyloxy) methylpyridinium-3-yl]phenylcarbamoyl]indoline chloride (E2)

5-Methoxy-6-trifluoromethyl-1-[3-fluoro-4-methyl-5-(pyridin-3-yl)phenyl carbamoyl]indoline (0.195 g, 0.44 mmol) was converted to the title compound (E2) according to the method of Example 1 to give a yellow solid (0.23 g, 95%) m.p. 212–4° C.

$^1$H NMR (250 MHz; DMSO) δ: 2.12 (3H, m), 2.17 (3H, s), 3.28 (2H, t, J=8 Hz), 3.84 (3H, s), 4.22 (2H, t, J=8 Hz), 6.49 (2H, s), 7.22 (1H, s), 7.60–7.70 (2H, m), 8.10 (1H, s), 8.36 (1H, dd, J=8 Hz, 7 Hz), 8.82 (1H, d, J=9 Hz), 9.11 (1H, s), 9.28 (1H, d, J=5 Hz), 9.49 (1H, s).

Mass spectrum (FAB) 518 (M+).

EXAMPLE 3

5,6-Dichloro-1-[6-[1-(acetyloxy)methyl-2-methylpyridinium-3-yl-oxy]pyridin-3-ylcarbamoyl]indoline chloride (E3)

5,6-Dichloro-1-[6-(2-methylpyridin-3-yloxy)pyridin-3-ylcarbamoyl]indoline (0.25 g, 0.6 mmol) was treated with bromomethyl acetate and sodium tetraphenylboron at reflux in acetonitrile (15 ml) for 10 h according to the procedure described in Example 1 to give the title compound (E3) (0.26 g, 80%) m.p. 125–135° C. which contained approximately 15% starting material as an off-white solid.

$^1$H NMR (200 MHz; DMSO) δ: 2.17 (3H, s), 2.79 (3H, s), 3.20 (2H, t, J=8 Hz), 4.22 (2H, t, J=8 Hz), 6.53 (2H, s), 7.32 (1H, d, J=9 Hz), 7.49 (1H, s), 8.02 (1H, s), 8.08 (1H, dd, J=8 Hz, 6 Hz), 8.20 (1H, dd, J=9 Hz, 3 Hz), 8.38 (1H, d, J=3 Hz), 8.56 (1H, d, J=8 Hz), 9.06 (1H, d, J=6 Hz), 9.12 (1H, s).

EXAMPLE 4

5-Methoxy-6-trifluoromethyl-1-[3,4-difluoro-5-[1-(acetyloxymethyl)pyridinium-3-yl]phenylcarbamoyl]indoline chloride (E4)

5-Methoxy-6-trifluoromethyl-1-[3,4-difluoro-5-(pyridin-3-yl)phenylcarbamoyl]indoline (0.30 g, 0.67 mmol) was converted into the title compound (E4) according to the method of Example 1. The tetraphenylborate salt was stirred with Dowex 1×8-200 ion-exchange resin in 1:1 acetonitrile/2-propanol (25 ml) for 24 h. The resin was then filtered off and the filtrate evaporated to give the title compound (0.35 g, 94%), mp 201–2° C.

$^1$H NMR (250 MHz; $D_6$DMSO) δ: 2.17 (3H, s), 3.29 (2H, t, J=8 Hz), 3.84 (3H, s), 4.25 (2H, t, J=8 Hz), 6.51 (2H, s), 7.23 (1H, s), 7.89 (2H, m), 8.12 (1H, s), 8.39 (1H, t, (J=7 Hz), 8.96 (1H, d, J=7 Hz), 9.27 (1H, s), 9.32 (1H, d, J=7 Hz), 9.52 (1H, s).

Mass Spectrum (FAB) 522 (M+).

I claim:

1. A compound of formula (I):

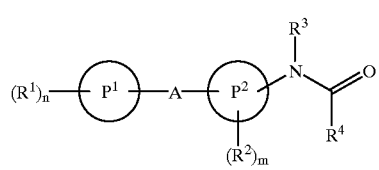

wherein:

$R^1$ and $R^2$ groups are each independently hydrogen, $C_{1-6}$ alkyl optionally substituted by $NR^{12}R^{13}$, $C_{2-6}$ alkenyl, $C_{2-6}$ alkynyl, $C_{1-6}$ alkylthio, cyano, nitro, halogen, $CF_3$, $C_2F_5$, $NR^{12}R^{13}$, $CONR^{12}R^{13}$, $NR^{12}COR^{13}$, $S(O)_p$ $NR^{12}R^{13}$, CHO, $OCF_3$, $SCF_3$, $COR^{14}$, $CH_2OR^{14}$, $CO_2R^{14}$ or $OR^{14}$ where p is 1 or 2 and $R^{12}$, $R^{13}$ and $R^{14}$ are independently hydrogen, $C_{1-6}$ alkyl, optionally substituted aryl or optionally substituted aryl$C_{1-6}$alkyl, or $R^1$ and $R^2$ are $N^+I^-R^{12}R^{13}CR^{12}R^{13}OCOR^{14}$ where $R^{12}$, $R^{13}$ and $R^{14}$ are as defined above and $I^-$ is a counter ion;

n and m are independently 0, 1 or 2;

$R^3$ is hydrogen or $C_{1-6}$ alkyl;

$R^4$ is a group of formula (A):

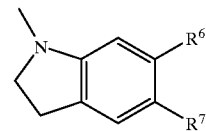

in which:

$R^6$ and $R^7$ are independently hydrogen, $C_{1-6}$ alkyl optionally substituted by one or more fluorine atoms, $C_{2-6}$ alkenyl, $C_{3-6}$ cycloalkyl, $C_{3-6}$ cycloalkyl$C_{1-6}$alkoxy, $C_{2-6}$ alkynyl, $C_{3-6}$ cycloalkyloxy, $C_{3-6}$ cycloalkyl-$C_{1-6}$ alkyl, $C_{1-6}$ alkylthio, $C_{3-6}$ cycloalkylthio, $C_{3-6}$ cycloalkyl-$C_{1-6}$ alkylthio, $C_{1-6}$alkoxy, hydroxy, halogen, nitro, $OCF_3$, $SCF_3$, $SO_2CF_3$, $SO_2F$, formyl, $C_{2-6}$ alkanoyl, cyano, optionally substituted phenyl or thienyl, $NR^{12}R^{13}$, $CONR^{12}R^{13}$ or $CO_2R^{14}$ where $R^{12}$, $R^{13}$ and $R^{14}$ are as defined above; or $R^6$ and $R^7$ form part of an optionally substituted 5- or 6-membered carbocyclic or heterocyclic ring;

$R^9$ and $R^{10}$ are independently hydrogen or $C_{1-6}$ alkyl;

A is a bond, or a group$(CH_2)_p$E, or $E(CH_2)_p$, optionally substituted by $C_{1-6}$ alkyl, wherein p is 1 to 4 and E is CO, O or $S(O)_x$ wherein x is 0 to 2, or A is NR, CONR, NRCO, NRCONR, CO, CH(OH), $C_{1-6}$alkyl, CH=CH, CH=CF, O, $S(O)_x$ where x is 1 or 2, $NRSO_2$ where R is hydrogen or $C_{1-6}$ alkyl;

or A is an optionally substituted phenyl or an optionally substituted 5- to 7-membered heterocyclic ring containing up to three heteroatoms selected from nitrogen, oxygen or sulphur;

$P^1$ is phenyl or a group of formula (B):

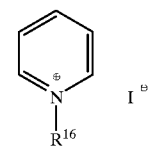

wherein:

$R^{16}$ is $C_{1-6}$ alkyl, $C_{1-6}$ alkoxy, oxygen, $NR^{17}R^{18}$, $NHCONR^{17}R^{18}$, $NHCOR^{19}$, $CR^{17}R^{18}OCOR^{19}$, $OCR^{17}R^{18}OCOR^{19}$, $CR^{17}R^{18}OCONR^{17}R^{18}$, or $OCR^{17}R^{18}$ $OCONR^{17}R^{18}$ where $R^{17}$, $R^{18}$ and $R^{19}$ are independently hydrogen, $C_{1-20}$ alkyl, optionally substituted aryl or optionally substituted aryl$C_{1-6}$alkyl and $I^-$ is a counter ion; and $P^2$ is phenyl or pyridyl;

provided that at least one of $R^1$, $R^2$ or $P^1$ forms a quaternary ammonium group.

2. A compound according to claim 1 in which $P^1$ is a group of formula (B) and $R^{16}$ is a group $CR^{17}R^{18}OCOR^{19}$.

3. A compound according to claim 1 where A is a bond or O.

4. A compound according to claim 1 where the counter ion is a halogen.

5. A compound according to claim 1 which is:

5-Methoxy-6-trifluoromethyl-1-[3-fluoro-5-[1-(acetyloxy)methyl-pyridinium-3-yl]phenylcarbamoyl]indoline chloride, 5-Methoxy-6-trifluoromethyl-1-[3-fluoro-4-methyl-5-[1-(acetyloxy)methylpyridinium-3-yl]phenylcarbamoyl] indoline chloride, 5,6-Dichloro-1-[6-[1-(acetyloxy)methyl-2-methylpyridinium-3-yl-oxy]pyridin-3-ylcarbamoyl] indoline chloride, or 5-Methoxy-6-trifluoromethyl-1-[3,4-difluoro-5-[1-(acetyloxymethyl)pyridinium-3-yl]phenylcarbamoyl] indoline chloride.

6. A pharmaceutical composition comprising a compound according to claim 1 and a pharmaceutically acceptable excipient.

7. A process for preparing a compound of claim 1 in which $P^1$ is a group of formula (B) which comprises reacting a compound of a compound of formula (II):

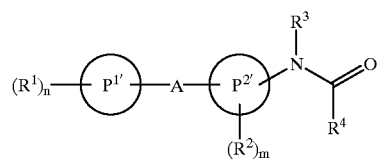

(II)

in which A, $R^1$, $R^2$, $R^3$, $R^4$, n and m are as defined in claim 1 and $P^{1'}$ is pyridyl, and $P^{2'}$ has the meaning of $P^2$ as defined in claim 1, with a compound of formula (III):

$$I—R^{16} \qquad (III)$$

in which $R^{16}$ is as defined in claim 1 and I is such that $I^-$ is a leaving group that forms the counter ion as defined in claim 1.

* * * * *